United States Patent [19]

Pohlke

[11] 4,049,659
[45] Sept. 20, 1977

[54] PROCESS FOR THE PREPARATION OF 4-OXO-HEXAHYDRO-PYRAZINOISOQUINOLINE DERIVATIVES

[75] Inventor: Rolf Pohlke, Darmstadt, Germany

[73] Assignee: Merck Patent Gesellschaft mit beschrankter, Darmstadt, Germany

[21] Appl. No.: 662,009

[22] Filed: Feb. 27, 1976

[30] Foreign Application Priority Data

Mar. 1, 1975 Germany .............................. 2508947

[51] Int. Cl.$^2$ ......................................... C07D 471/04
[52] U.S. Cl. ............................. 260/268 TR; 424/250
[58] Field of Search .................................. 260/268 TR Primary Examiner—Donald G. Daus
Assistant Examiner—Jose Tovar
Attorney, Agent, or Firm—Millen & White

[57] ABSTRACT

4-oxo-hexahydro-pyrazinoisoquinoline derivatives are obtained in good yield by a single-step process which comprises hydrolyzing a 2-acyl-4-oxo-1,2,3,6,7,11b-hexahydro-4H-pyrazino[2,1-a]isoquinoline with an oxygen-containing acid or acid salt of inorganic pentavalent phosphorus or hexavalent sulfur.

10 Claims, No Drawings

PROCESS FOR THE PREPARATION OF 4-OXO-HEXAHYDRO-PYRAZINOISOQUINO-LINE DERIVATIVES

BACKGROUND OF THE INVENTION 4-oxo-hexahydro-pyrazinoisoquinoline derivatives of the general formula I

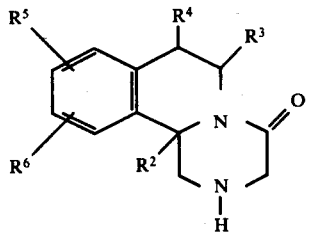

I wherein $R^2$, $R^3$ and $R^4$ are each H or methyl and $R^5$ and $R^6$ are each H, methyl or methoxy, as well as their physiologically compatible acid addition salts, can be converted by acylation into the corresponding 2-acyl-4-oxo-1,2,3,6,7,11b-hexahydro-4H-pyrazino[2,1-a]isoquinolines with anthelmintic effectiveness and thus are important intermediate products. The compounds of Formula I are also themselves effective as anthelmintics.

In published German Patent Specification No. 23,31,713, corresponding to copending, commonly assigned U.S. Pat. application Ser. No. 481,792 filed June 24, 1974 and now U.S. Pat. No. 3,993,760, the contents of which are incorporated by reference herein, there is described a two-stage process for the preparation of 4-oxo-1,2,3,6,7,11b-hexahydro-4H-pyrazino[2,1-a]isoquinoline which starts from 2-benzoyl-4-oxo-1,2,3,6,7,11b-hexahydro-4H-pyrazino[2,1-a]isoquinoline. In the first reaction stage of this process, the benzoyl radical is split off by hydrolysis while the lactam ring is simultaneously split so that N-(1,2,3,4-tetrahydroisoquinolyl-1-methyl)-glycine results. The lactam ring is subsequently closed in the second reaction stage by heating. Yields are on the order of 70–80%.

OBJECTS OF THE INVENTION

It is a general object of the present invention to provide an economical process for the preparation of 4-oxo-1,2,3,6,7,11b-hexahydro-4H-pyrazino[2,1-a]isoquinoline and of its derivatives of Formula I.

Upon study of the specification and appended claims, further objects and advantages of this invention will become apparent to those skilled in the art.

SUMMARY OF THE INVENTION

Briefly, the above and other objects are attained in one aspect of this invention by providing, in a process for preparing a 4-oxo-hexahydro-4H-pyrazinoisoquinoline derivative of the formula

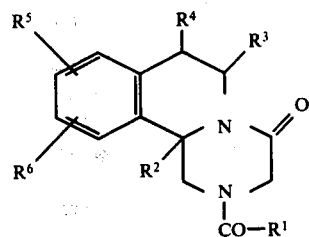

wherein $R^2$, $R^3$ and $R^4$ are each H or methyl and $R^5$ and $R^6$ are each H, methyl or methoxy, as well as the physiologically compatible acid addition salts thereof, the improvement which comprises: hydrolyzing a 2-acyl-4-oxo-1,2,3,6,7,11b-hexahydro-4H-pyrazino[2,1-a]isoquinoline of the formula

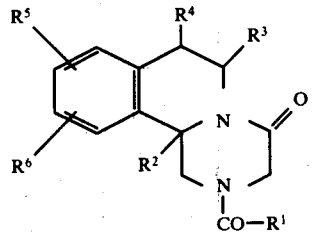

wherein $R^1$ is H, alkyl of 1–5 carbon atoms, phenyl or phenyl substituted by one or more alkyl or alkoxy of up to 4 carbon atoms or by halogen, with an oxygen-containing acid of pentavalent phosphorus or of hexavalent sulfur or an acid salt thereof to form said 4H-pyrazinoisoquinoline derivative.

DETAILED DISCUSSION

It has unexpectedly been found that compounds of Formula I can be prepared in a one-stage process by hydrolyzing a 2-acyl-4-oxo-1,2,3,6,7,11b-hexahydro-4H-pyrazino[2,1-a]-isoquinoline of the general Formula II

II wherein $R^1$ is H, a straight-chained or branched alkyl radical having 1–5 carbon atoms, or a phenyl radical optionally substituted by one or more alkyl or alkoxy of up to 4 carbon atoms or by halogen, with an oxygen-containing acid of pentavalent phosphorus or of hexavalent sulfur or an acid salt of these acids.

The course of this reaction was not to be expected. To the contrary, it ought to be assumed that also with the reagents according to the invention, the lactam ring would also open with the simultaneous splitting off of the acyl group. Thus, as products of the hydrolysis, the corresponding bicyclic 1-carboxymethylaminomethyl-1,2,3,4-tetrahydroisoquinoline derivatives or mixtures thereof with compounds of Formula I and/or with starting materials of Formula II were to be expected. In contradistinction thereto, the hydrolysis according to the present invention proceeds selectively and gives compounds of Formula I in high yields.

Consequently, the subject of the invention is a new, advantageous process for the preparation of the 4-oxo-hexahydro-4H-pyrazino-isoquinolines of Formula I, as well as of their physiologically compatible acid addition salts, which is characterized by hydrolyzing a compound of Formula II with an oxygen-containing acid of pentavalent phosphorus or of hexavalent sulphur or an acid salt of these acids.

The compounds of Formulae I and II each include not only the racemates but also the optical isomers. Thus, e.g. the laevorotary antipode of 2-benzoyl- or 2-acetyl-4-oxo-1,2,3,6,7,11b-hexahydro-4H-pyrazino[2,1-a]isoquinoline can be converted, according to the process of the present invention, into the laevorotary 4-oxo-1,2,3,6,7,11b-hexahydro-4H-pyrazino[2,1-a]isoquinoline.

Amongst the process products of Formula I, those are preferred in which $R^2$, $R^5$ and $R^6$ are H and $R^3$ or $R^4$ is each H or methyl.

The radical $R^1$ in Formula II is preferably straight-chained alkyl with 1-3 carbon atoms, especially methyl, or phenyl. However, $R^1$ can, inter alia, also signify H, straight-chained alkyl with 4 or 5 carbon atoms, branched alkyl with 3-5 carbon atoms or a phenyl radical optionally substituted one or more times, especially o-, m- or p-tolyl; 2,4-, 3,4- or 3,5-dimethylphenyl; o-, m- or p-methoxyphenyl; 2,4-, 3,4- or 3,5-dimethoxyphenyl; or 2,4,6- or 3,4,5-trimethoxyphenyl. When $R^1$ stands for a phenyl radical substituted by halogen, fluorophenyl and chlorophenyl are preferred, e.g. o-, m- or p-fluorophenyl, o-, m- or p-chlorophenyl, 2,4-difluorophenyl and 2,4-dichlorophenyl.

Suitable oxygen-containing acids of pentavalent phosphorus or of hexavalent sulfur include but are not limited to orthophosphoric acid $H_3PO_4$, diphosphoric acid $H_4P_2O_7$, the water-poorer polyphosphoric acids $(HPO_3)_n$ ($n > 2$), as well as the metaphosphoric acids $H_3P_3O_9$ and $H_4P_4O_{12}$, sulfuric acid $H_2SO_4$ and disulfuric acid $H_2S_2O_7$. Of the phosphoric acids, orthophosphoric acid, e.g. 50-100%, especially 85-100%, phosphoric acid, is preferred. Of the sulfur acids, outstandingly suitable are concentrated sulfuric acid solutions, e.g. 90-100%, especially 98%, sulfuric acid. Preferred acid salts are the alkali metal salts, e.g. those of sodium, potassium or lithium. Especially suitable are the primary phosphates $NaH_2PO_4$ or $KH_2PO_4$, sodium hydrogen sulfate and, especially, potassium hydrogen sulfate.

The starting material is advantageously finely powdered before the reaction and the reaction mixture is kept well stirred and/or vigorously boiled. The reaction is preferably carried out with equimolar amounts of acid or with a small excess of acid; however, large amounts of acid can also be employed. The reaction preferably takes place in the presence of water. Aqueous-alcoholic solutions can also be employed, with methanol and ethanol mainly suitable as alcohols.

One preferably works at normal pressure. However, for the careful treatment of the substances, it is also possible to carry out the reaction under reduced pressure, e.g. at about 2-25 mm.Hg., especially when highly concentrated acid is employed and/or when working at comparatively high temperatures. According to this reaction variant, the liberated acid of the formula $R^1COOH$ can easily be removed by distillation or sublimation from the reaction mixture. In this way, the chemical equilibrium is displaced in favor of the product of Formula I.

Temperature and time can be varied within wide limits. In the cases using phosphorus acids, the reaction temperatures lie approximately between 80° and 200° C., preferably between 100° and 150° C. After about 0.5 to 72, preferably 2 to 48 hours, the reaction is ended. If sulfuric acid is employed, then one expediently maintains the temperature between 80° and 150° C., preferably at about 100° C. and allows the reaction to proceed for about 2-6, preferably about 5, hours.

The reaction can also be carried out with the acid salts of the said acids. Here, too, one can work in aqueous or aqueous-alcoholic solution. Reaction temperatures with the acid salts generally lie between about 20° and 100° C., preferably between 80° and 100° C. The reaction times vary — according to the temperature— between 10 minutes and 3 days but are usually about 10 to 15 hours.

The compounds of Formula I can, by treatment with an acid, especially a physiologically compatible acid, be converted into their acid addition salts, e.g. into their hydrochlorides, sulfates, citrates, methane sulfonates, etc.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius; unless otherwise indicated, all parts and percentages are by weight.

EXAMPLE 1

1.5 g. 2-benzoyl-4-oxo-1,2,3,6,7,11b-hexahydro-4H-pyrazino[2,1-a]isoquinoline is heated with 1 g. 98% phosphoric acid for 2 days at 100° C. The reaction mixture is taken up in water and washed with chloroform. The aqueous solution is subsequently rendered alkaline and shaken out with chloroform. The chloroform solution is dried over sodium sulfate and evaporated. After the addition of ether, 4-oxo-1,2,3,6,7,11b-hexahydro-4H-pyrazino[2,1-a]isoquinoline crystallizes out; m.p. 119°-120° C.; yield 92%. Hydrobromide, m.p. 201° C.

The same reaction can be carried out by heating the starting material with 98% phosphoric acid for 2 hours at 150° C., whereby similar results are obtained.

EXAMPLE 2

4 g. 2-(3,4,5-trimethoxybenzoyl)-4-oxo-6-trans-methyl-1,2,3,6,7,11b-hexahydro-4H-pyrazino[2,1-a]isoquinoline is prepared from 1-cyano-2-(3,4,5-trimethoxybenzoyl)-1,2-dihydroisoquinoline by hydrogenation, subsequent reaction with chloroacetyl chloride and ring closure of the resultant 1-[(3,4,5-trimethoxybenzoyl)-aminomethyl]-2-chloroacetyl-1,2,3,4-tetrahydroisoquinoline with potassium tert.-butylate and reacted with 5 g. 98% phosphoric acid for 12 hours at 100° C. After cooling, the reaction mixture is taken up in 100 ml. water and washed with chloroform. The aqueous phase is rendered alkaline and subsequently extracted with chloroform. After drying the combined chloroform extracts with sodium sulfate followed by evaporation, 4-oxo-6-trans-methyl-1,2,3,6,7,11b-hexahydro-4H-pyrazino[2,1-a]isoquinoline, m.p. 135°–136° C., is obtained in 92% yield (from ethyl acetate).

EXAMPLE 3

(−)-2-benzoyl-4-oxo-1,2,3,6,7,11b-hexahydro-4H-pyrazino[2,1-a]isoquinoline is prepared from (±)-1-cyano-2-benzoyl-1,2,3,4-tetrahydroisoquinoline by hydrogenating in the presence of Raney nickel, optical splitting of the (±)-N-(1,2,3,4-tetrahydroisoquinoline-1-methyl)-benzamide obtained with (+)-tartaric acid, reaction of the (+)-antipode ([α]$_D^{20}$ = +27.0°) with chloroacetyl chloride and intramolecular ring closure of the (+)-N-(2-chloroacetyl-1,2,3,4-tetrahydroisoquinoline-1-methyl)-benzamide obtained in the presence of butyl lithium.

Analogously to Example 1, from 1.5 g. (−)-2-benzoyl-4-oxo-1,2,3,6,7,11b-hexahydro-4H-pyrazine[2,1-a]isoquinoline and 1 g. 98% phosphoric acid, there is obtained (−)-4-oxo-1,2,3,6,7,11b-hexahydro-4H-pyrazino-[2,1-a]isoquinoline; m.p. 120° C., [α]$_D^{20}$ = −306° (in ethanol).

EXAMPLE 4

146 g. 2-benzoyl-4-oxo-1,2,3,6,7,11b-hexahydro-4H-pyrazino[2,1-a]isoquinoline and 153 g. 89% phosphoric acid are heated and stirred for 48 hours at 120° C. after the mixture has become liquid. The cooled mixture is taken up in 2 liters of water and shaken out with chloroform. The aqueous phase is subsequently adjusted with concentrated aqueous sodium hydroxide solution to pH 12 and shaken out with chloroform. The combined chloroform solutions are dried over sodium sulfate, purified with active charcoal and evaporated. 4-oxo-1,2,3,6,7,11b-hexahydro-4H-pyrazine[2,1-a]isoquinoline of m.p. 119°–120° C. is obtained in a yield of 98.5%.

From the correspondingly ring-substituted 2-benzoyl-4-oxo-1,2,3,6,7,11b-hexahydro-4H-pyrazino[2,1-a]isoquinolines, there are prepared analogously, by hydrolysis with 89% phosphoric acid, the following compounds: 4-oxo-6-cis-methyl-1,2,3,6,7,11b-hexahydro-4H-pyrazino[2,1-a]isoquinoline, m.p. 119°–120° C.; yield 95%.

4-oxo-6-trans-methyl-1,2,3,6,7,11b-hexahydro-4H-pyrazino-[2,1-a]isoquinoline, M.P. 135°–136° C; yield 97.5%.

EXAMPLE 5

12.2 g. of 2-acetyl-4-oxo-1,2,3,6,7,11b-hexahydro-4H-pyrazino[2,1-a]isoquinoline is prepared from 1-cyano-2-acetyl-1,2-dihydroisoquinoline by hydrogenation, subsequent reaction with chloroacetyl chloride and ring closure of the resultant 1-acetylaminomethyl-2-chloroacetyl-1,2,3,4-tetrahydroisoquinoline with potassium tert.-butylate, heated with 7.3 g. 89% phosphoric acid to 120° C. and stirred for 8 hours at the same temperature. The cooled mixture is taken up in water and washed with chloroform. The aqueous phase is thereupon adjusted with concentrated aqueous sodium hydroxide solution to pH 12 and shaken out with chloroform. The combined chloroform extracts are dried over sodium sulfate and evaporated. 4-oxo-1,2,3,6,7,11b-hexahydro-4H-pyrazino[2,1-a]isoquinoline of m.p. 119°–120° C. is obtained in a yield of 93%.

EXAMPLE 6

1.5 g. of 2-benzoyl-4-oxo-1,2,3,6,7,11b-hexahydro-4H-pyrazino[2,1-a]isoquinoline is heated with 1 g. 98% sulfuric acid for 5 hours at 100° C. and worked up analogously to Example 1. 4-oxo-1,2,3,6,7,11b-hexahydro-4H-pyrazino[2,1-a]isoquinoline; m.p. 119°–120° C. (from benzene) is obtained in a yield of 87%.

EXAMPLE 7

1. g. of 2-benzoyl-4-oxo-1,2,3,6,7,11b-hexahydro-4H-pyrazino[2,1-a]isoquinoline is boiled with 20 ml. concentrated potassium hydrogen sulfate solution for 48 hours. The solution is subsequently extracted with chloroform, and the organic phase is dried with sodium sulfate and evaporated. 4-oxo-1,2,3,6,7,11b-hexahydro-4H-pyrazino[2,1-a]isoquinoline of m.p. 119°–120° C. is obtained in a yield of 91%.

EXAMPLE 8 to 5 g. 4-oxo-6-trans-methyl-1,2,3,6,7,11b-hexahydro-4H-pyrazino[2,1-a]isoquinoline (prepared according to Example 2) and 6 ml. triethylamine in 100 ml. chloroform is added 5.5 g. 3-nitrobenzoyl chloride in 100 ml. chloroform, whereby the temperature increases to 50° C. After 1 hour, water is added thereto, the mixture extracted with chloroform, the chloroform extract washed with water, dried over sodium sulfate, filtered and evaporated. 2-(3-nitrobenzoyl)-4-oxo-6-trans-methyl-1,2,3,6,7,11b-hexahydro-4H-pyrazino[2,1-a]isoquinoline, m.p. 90°–92° C. is obtained in a yield of 91%.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. In a process for preparing a 4-oxo-hexahydro-4H-pyrazino-isoquinoline compound of the formula

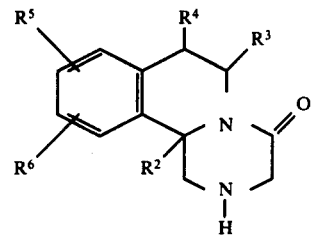

wherein $R^2$, $R^3$ and $R^4$ are each H or methyl and $R^5$ and $R^6$ are each H, methyl or methoxy, as well as the physiologically compatible acid addition salts thereof, the improvement which comprises:
hydrolyzing a 2-acyl-4-oxo-1,2,3,6,7,11b-hexahydro-4H-pyrazino[2,1-]isoquinoline of the formula

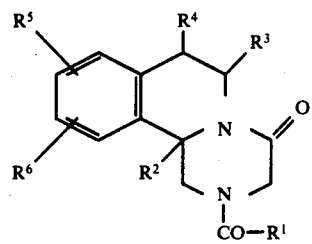

wherein $R^1$ is H, alkyl of 1-5 carbon atoms, phenyl or phenyl substituted by one or more alkyl or alkoxy of up to 4 carbon atoms or by halogen, with an oxygen-containing inorganic acid of pentavalent phosphorus or of hexavalent sulfur or with an acid salt thereof to form said 4H-pyrazino-isoquinoline derivative.

2. A process according to claim 1, wherein $R^2$, $R^5$ and $R^6$ are hydrogen, and $R^3$ and $R^4$ are each hydrogen or methyl.

3. A process according to claim 1, wherein $R^1$ is methyl, ethyl, n-propyl or phenyl.

4. A process according to claim 3, wherein $R^1$ is methyl.

5. A process according to claim 1, wherein said acid is 50-100% orthophosphoric acid.

6. A process according to claim 1, wherein said acid is 90-100% sulfuric acid.

7. A process according to claim 1, wherein said acid is a monobasic alkali metal acid salt of $H_3PO_4$ or $H_2SO_4$.

8. A process according to claim 7, wherein the acid salt is potassium hydrogen sulfate.

9. A process according to claim 1, wherein the reaction is conducted in an aqueous alcoholic solvent.

10. A process according to claim 9, wherein $R^2$, $R^5$ and $R^6$ are hydrogen, $R^3$ and $R^4$ are each hydrogen or methyl, $R^1$ is methyl, ethyl, n-propyl or phenyl and the acid is 85-100% orthophosphoric acid, 98% sulfuric acid or potassium hydrogen sulfate.

* * * * *